(12) United States Patent
Lee et al.

(10) Patent No.: US 7,358,337 B2
(45) Date of Patent: Apr. 15, 2008

(54) ASSAY FOR LOW MOLECULAR WEIGHT HEPARIN

(75) Inventors: Ted C. K. Lee, Matawan, NJ (US); Amanda B. McBride, Turnersville, NJ (US); Frank M. LaDuca, East Brunswick, NJ (US)

(73) Assignee: International Technidyne Corporation, Edison, NJ (US)

( * ) Notice: Subject to any disclaimer, the term of this patent is extended or adjusted under 35 U.S.C. 154(b) by 863 days.

(21) Appl. No.: 10/222,345

(22) Filed: Aug. 16, 2002

(65) Prior Publication Data

US 2004/0033551 A1 Feb. 19, 2004

(51) Int. Cl.
 *A61K 35/14* (2006.01)
(52) U.S. Cl. .................................................. 530/380
(58) Field of Classification Search ............. 530/350; 514/12
 See application file for complete search history.

(56) References Cited

U.S. PATENT DOCUMENTS

| | | | | |
|---|---|---|---|---|
| 5,314,695 A | * | 5/1994 | Brown | 424/450 |
| 5,625,036 A | | 4/1997 | Hawkins et al. | |
| 5,858,724 A | | 1/1999 | Novy et al. | 435/69.6 |
| 6,100,072 A | | 8/2000 | Brucato et al. | 435/69.7 |
| 6,183,979 B1 | | 2/2001 | Lee et al. | 435/13 |
| 6,194,394 B1 | | 2/2001 | Hawkins | |
| 6,403,381 B1 | | 6/2002 | Mann et al. | 436/69 |
| 2003/0104508 A1 | | 6/2003 | Gempeler et al. | |

FOREIGN PATENT DOCUMENTS

WO  WO 99/10746  3/1999

OTHER PUBLICATIONS

Besselaar, Blood Coagulation and Fibrinolysis, 6, p. 239-244 (1995).*
Nelsestuen, J. Biological Chemistry, 276, No. 43, p. 39825-39831 (2001).*
Miletich, *Prothrombin Time*, Williams Hematology, Fifth Edition, 1995; L82-L84.
Miletich, *Activated Partial Thromboplastin Time*, Williams Hematology, Fifth Edition, 1995; L85-L86.
Schultz et al., *The Influence of Heparin on the Prothrombin Time*, Pharmacotherapy, vol. 11, No. 4, 1991; 312-316.
Holmes et al., *Novel, Bedside, Tissue Factor—Dependent Clotting Assay Permits Improved Assessment of Combination Antithrombotic and Antiplatelet Therapy*, Circulation, 2000; 2051-2057.
Lawson et al., *Cooperative Activation of Human Factor IX by the Human Extrinsic Pathway of Blood Coagulation*, The Journal of Biological Chemistry, vol. 266, No. 17, 1991; 11317-11327.
Mize et al., *Rapidpoint™ Coag Enoxaparin Test: Clinical Results for a POC Method for Monitoring Lovenox® (Enoxaparin Sodium) in Patients Undergoing PCI*, American Society of Hematology 43rd Annual Meeting and Exposition, 2001; 193.
Mize et al., *Development of the Rapidpoint™ Coag Enoxaparin Test System to Monitor Lovenox® (Enoxaparin Sodium) in PCI Patients*, American Society of Hematology 43rd Annual Meeting and Exposition, 2001; 185.
Harenberg et al., Blood Coagulation and Fibrinolysis, 7:453-458 (1996).

* cited by examiner

*Primary Examiner*—Karen Cochrane Carlson
*Assistant Examiner*—Agnes B. Rooke
(74) *Attorney, Agent, or Firm*—Synnestvedt & Lechner

(57) ABSTRACT

A prothrombin time reagent for determination of low molecular weight heparin in frsh whole blood and in anticoagulant treated blood is provided. The reagent is composed of recombinant animal tissue factor, and a mixture of synthetic phospholipids, which mixture includes a phosphatidylalcohol. A formulation buffer which includes a sensitivity adjuster is used in formulating the reagent. The recombinant animal tissue factor includes rabbit brain. The synthetic phospholipids of the mixture include palmitoyloleoylphosphatidylcholine (POPC), palmitoyloleoyl-phosphatidylserine (POPS), and a phosphatidylalcohol. The phosphatidyl alcohol includes dioleoylphosphatidylethanol, dioleoylphosphatidylmethanol, dioleoylphosphatidylpropanol, dioleoylphosphatidylbutanol, and dioleoylphosphatidylinositol. The sensitivity adjuster included in the formulation buffer is γ-Cyclodextrin. The formulated reagent is air-dried and remains stable for at least 3 weeks at 37° C.

13 Claims, No Drawings

ASSAY FOR LOW MOLECULAR WEIGHT HEPARIN

FIELD OF THE INVENTION

The present invention relates generally to assays for determining the concentration of low molecular weight heparin in a blood sample.

BACKGROUND OF THE INVENTION

Blood coagulation tests may be performed for a variety of purposes, including determining the bleeding susceptibility of patients undergoing surgery, and monitoring patients undergoing anti-coagulation therapy for the prevention of blood clots. A variety of coagulation tests are presently in use, for example, the Activated Partial Thromboplastin Test (APTT), and Prothrombin Time (PT) test. Both tests measure clotting time to evaluate a patient's baseline hemostatic state or to monitor the response to anticoagulant therapy.

The APTT test is used for the evaluation of the intrinsic and common coagulation pathways, and for monitoring therapy with unfractionated heparin and other anticoagulants. The APTT measures the time in seconds required for a fibrin clot to form in a plasma sample to be tested after a partial thromboplastin reagent (an activating agent) and calcium chloride have been added to the sample. The APTT test is widely used for monitoring heparin therapy.

The PT test relies upon the induction of the extrinsic coagulation protease factor VIIa by thromboplastin in a blood sample to be tested. The extrinsic coagulation pathway results in the production of thrombin, a proteolytic enzyme that catalyzes the conversion of fibrinogen to fibrin, which is essential to the clotting process. The PT test utilizes this series of enzymatic events in vitro under controlled conditions to diagnose dysfunctions or deficiencies in the blood coagulation system of patients. The PT test is also used in determining a safe and effective dose of an anticoagulant. The amount of time (in seconds) that elapses until clot formation occurs is the Prothrombin Time, or PT value.

Anticoagulant therapy for acute thromboembolic disease typically consists of parenteral heparin followed by oral warfarin. The pharmacodynamic properties of warfarin necessitate a period of overlapping therapy with heparin until a steady-state warfarin anticoagulant effect is achieved. Heparin (unfractionated) is a polysaccharide with sulfate groups attached by covalent bonding. Heparin is heterogenous in terms of molecular weight and the degree of sulfation. The molecular weight ranges between about 5,000 to about 30,000 daltons. The anti-coagulant effect of heparin in blood results from the binding and activation of a plasma protein, antithrombin III (AT III), which inhibits enzymes in the coagulation cascade. In particular, the heparin-AT III complex inhibits the coagulation activity of Factors Xa and IIa (thrombin). R. D. Rosenberg et al., Hemostasis and Thrombosis, ed. R. Colman et al., p. 711 (2001). An infusion of excess heparin in a patient, however, may cause bleeding problems.

The administration of heparin is typically monitored using the Activated Partial Thromboplastin Time (APTT) assay. The APTT assay generally consists of three steps: 1) addition of an activator to plasma or blood; 2) incubation of two to four minutes; and, 3) addition of calcium chloride solution, after which the clotting time is monitored. The APTT assay provides a prolonged clot time in the presence of heparin. As an alternative to the APTT assay, a one-step prothrombin time (PT) assay has been investigated. A coagulation assay system using a PT reagent is a simpler and faster method requiring only one reagent (PT), and does not require incubation time, as opposed to an APTT system for heparin which requires two reagents (activating agent and calcium chloride) and two to five minutes for incubation. J. P. Miletich, Prothrombin Time, Williams Hematology, Fifth Ed., Ed. by E. Beutler, pp. L82-L86 (1995a and 1995b).

With regard to a PT system for assaying heparin, Schultz et al. reported that the clotting time difference between 0.2 and 0.4 units per ml of heparin (therapeutic range) in citrated plasma is only a few seconds. N. J. Schultz, et al., The Influence of Heparin on the Prothrombin Time, Pharmacotherapy, Vol. 11, No. 4, pp 312-316 (1991). The clotting time separation of only a few seconds, however, is too narrow for the measurement of heparin levels in plasma or a blood sample to use a PT reagent.

Low molecular weight heparin (LMWH), as an alternative to standard heparin, is derived from unfractionated heparin through either chemical or enzymatic depolymerization. R. J. Linhardt et al., Semin. Thromb. Hemost. Suppl., 3, pp.5-16 (1999). LMWH has a molecular weight ranging from about 3,000 to about 4,500 daltons. The difference in molecular weight results in properties that are distinct from those of standard or traditional heparin. For example, LMWH binds less strongly to protein, has enhanced bioavailability, and interacts less with platelets. As with standard heparin, LMWH binds to antithrombin III, but inhibits thrombin to a lesser degree (and Factor Xa to a greater degree) than standard heparin. LMWH is increasingly being used in patients with unstable angina, deep vein thrombosis, and percutaneous coronary intervention.

The activity of LMWH may be expressed in terms of anti-Xa activity. The anti-Xa activity of LMWH in patient blood samples is usually determined by chromogenic assay with the isolated plasma. This is a time consuming assay using an expensive procedure. In recent publications, LMWH has been described as having significant anti-IIa activity, L. Bara et al., Thromb. Res., 69,443-452 (1993), as accumulating in patients of renal failure, M. Samama, Thromb. Haemost., 15, 199 (1995), and as causing bleeding problems in some patients involving surgery to the knee and hip, Shaieb, M. D., et al., J. Arthroplasty, 14, 432-438 (1999), and to the spine, Lumpkin, M. M., Int. J. Trauma Nurs., 4, 56-57 (1998). Hence, there is an increasing demand in the medical field for monitoring the effects of LMWH.

Holmes, et al., reported on low molecular weight heparin determination by PT assay, showing a good separation of clotting times between control blood and therapeutic range (0.6 to 1.0 u/ml) of a blood sample treated with Enoxaparin, a low molecular weight heparin preparation available from Aventis Corporation. Enoxaparin is also available, under the trademark LOVENOX®, from Aventis Corporation. In the system described by Holmes, et al., the clotting time for 1.0 u/ml of Enoxaparin is above 400 seconds, and an expensive corn trypsin inhibitor is required due to the lengthy clotting times, i.e., 272 to 486 seconds. M. B. Holmes, et al., Novel, Bedside, Tissue Factor-Dependent Clotting Assay Permits Improved Assessment of Combination Antithrombotic and Antiplatelet Therapy, Circulation, 102, pp.2051-2057 (2000).

A method of monitoring LMWH in a citrated plasma sample by prothrombin time assay was described by Wu in WO 99/10746. In the Wu method, commercially available thromboplastin (PT reagent) was used by diluting 200 to 6,400-fold in buffered calcium chloride solution, followed by mixing with citrated plasma for the clotting assay. The composition and process of preparation of the commercially available thromboplastin, however, were not disclosed. The reagent described by Wu is a liquid state reagent.

An air-dried PT reagent for the assay of plasma prothrombin time is described by Lee et al., in U.S. Pat. No. 6,183,979, assigned to the assignee herein, the entire disclosure of which is hereby incorporated by reference, but the PT reagent described is not suitable for monitoring low molecular weight heparin.

There remains a need for a highly sensitive and stable reagent and assay for measuring the concentration of low molecular weight heparin in blood.

SUMMARY OF THE INVENTION

Briefly described, a prothrombin time reagent for determining the concentration of low molecular weight heparin in fresh whole blood and anticoagulant-treated blood includes a recombinant animal tissue factor, and a mixture of synthetic phospholipids including a selected phosphatidylalcohol, which mixture lipidates said recombinant animal tissue factor to form a lipidated tissue factor. The reagent further includes a buffer solution. The recombinant animal tissue factor includes rabbit brain, which is present in an amount of about 4 µg/ml to about 6 µg/ml.

The mixture of synthetic phospholipids includes palmitoyloleoylphosphatidylcholine (POPC) and palmitoyoleoylphosphatidylserine (POPS). The phosphatidylalcohol is selected from dioleoylphosphatidylethanol, dioleoylphosphatidylmethanol, dioleoylphosphatidylpropanol, dioleoylphosphatidylbutanol, and dioleoylphosphatidylinositol. The mixture of POPC, POPS, and said selected phosphatidylalcohol is added to the reagent at a concentration ratio of 70:10-20:10-20. The reagent also includes a buffer solution, including Hepes, sodium chloride; gamma-cyclodextrin; beta-alanine; serine; sorbitol; bovine serum albumin; phenol; and, butylated hydroxytoluene. Exposing the reagent to an atmosphere of about 5% to about 10% relative humidity at about 20° C. to about 37° C. for about two hours thereby forms an air-dried reagent that is stable for at least three weeks at a temperature of about 37° C.

The invention also includes a prothrombin time reagent for determining the concentration of low molecular weight heparin in fresh whole blood and anticoagulant-treated blood, which includes a recombinant animal tissue factor, a mixture of synthetic phospholipids including a selected phosphatidylalcohol, which mixture lipidates the tissue factor to form a liposome complex, and a buffer solution comprising a sensitivity adjuster. The sensitivity adjuster includes an aldehyde free gamma-cyclodextrin, a derivative thereof, or an analog thereof, and the buffer solution includes Hepes, sodium chloride, beta-alanine, serine, sorbito, bovine serum albumin, phenol, and, butylated hydroxytoluene. The sensitivity adjuster may be present in an amount of about 1% by weight of the reagent. Exposing the reagent to an atmosphere of about 5% to about 10% relative humidity at about 20° C. to about 37° C. for about two hours thereby forms an air-dried reagent that is stable for at least three weeks at a temperature of about 37° C.

The invention also includes a method for preparing an air-dried prothrombin time reagent, which is formed by providing a recombinant animal tissue factor, providing a mixture of synthetic phospholipids, selecting a phosphatidylalcohol, adding the selected phosphatidylalcohol to the mixture thereby forming a lipid mixture, which composition is present in an effective amount to lipidate said recombinant animal tissue factor to form a lipidated tissue factor. The recombinant animal tissue factor is combined with the lipid mixture to form a lipidated tissue factor solution, to which a formulation buffer solution including a sensitivity adjuster is added to the lipidated tissue factor solution to form a liquid reagent. The liquid reagent is dried for about two hours in an atmosphere of about 5% relative humidity, and at about 20° C. to about 37° C. to form an air-dried reagent that remains stable for at least three weeks at a temperature of about 37° C.

The invention also includes a method for determining prothrombin time in a patient, which includes providing a sample of blood, reacting the sample of blood with a reagent according to an aspect of the invention for determining prothrombin time, and measuring the time it takes for a clot to form. The reagents and methods of the invention may be used for determining the concentration of low molecular weight heparin, such as Enoxaparin, and Dalteparin.

DETAILED DESCRIPTION OF THE INVENTION

The prothrombin time reagents and methods of the present invention employ an recombinant animal tissue factor and a mixture of synthetic phospholipids including a phosphatidylalcohol for determining the concentration of low molecular weight heparin in a blood sample. The reagent may be air-dried, without the need for lyophilization. The reagents and methods are suitable for assaying the therapeutic range of LMWH in anti-coagulant treated blood and plasma, and fresh whole blood. The therapeutic range of a LMWH capable of being assayed with the reagents and methods of the invention, for example, Enoxaparin and Dalteparin, is 0.6 to 1.0 u/ml, whereas the therapeutic range of unfractionated heparin is 0.2 to 0.4 u/ml. Dalteparin is sold under the trademark FRAGMIN®, and is available from Pharmacia Upjohn Corporation.

Preferably, an animal recombinant tissue factor derived from rabbit brain is employed in the invention. A suitable r-TF derived from rabbit brain is available as a clear solution from Pel Freeze, Inc. of Rogers, Ark., which is characterized as an apoprotein consisting of a fusion molecule of approx 45 Kd, containing extracellular and transmembrane domains of tissue factor, plus an amino terminal leader sequence consisting of several domains including a bacterial protein thioredoxin which aid in expression and purification. The thioredoxin rTF conjugate has a greater solubility than rTF, which aid in handling of the protein. U.S. Pat. No. 5,858,724 to Novy, et al., titled "Recombinant Rabbit Tissue Factor", issued Jan. 12, 1999, contains a further description of a suitable r-TF, the entire disclosure of which is hereby incorporated by reference.

Preferably, the relatively low concentration of the r-TF present in the reagent according to an aspect of the invention ranges between about 3 µg/ml to about 7 µg/ml, and more particularly, between about 4 µg/ml to about 6 µg/ml to obtain a desired sensitivity. The recombinant animal tissue factor is combined with a mixture of synthetic phospholipids including a phosphatidylalcohol, which mixture has been solubilized in a solution containing a suitable detergent, for example, octylglucoside. The mixture of synthetic phospholipids, preferably, palmitoyloleoylphosphatidylcholine (POPC) and palmitoyloleoylphosphatidylserine (POPS), includes a selected phosphatidylalcohol. The preferred synthetic lipids (POPC AND POPS) employed in the invention have been described by J. H. Lawson and K. G. Mann, J. Biol., Chem., 266, 11317 (1991). Synthetic phospholipids are preferred, as they provide a more reproducible final product since the chemical composition is more defined and therefore more consistent than natural phospholipids. The functional activity of the reagent is also easier to control due to the side chain variations of the synthetic phospholipids.

Synthetic phospholipids, including phosphatidylalcohols, are each available from Avanti Corporation, of Alabaster, Ala. Synthetic phospholipids, which are conveniently obtained from the manufacturer in ampoule form, containing 25 mg each, are mixed together in a suitable ratio for the present composition. The synthetic phospholipids utilized in the invention may have variations in the fatty acid side chains that are not found in naturally occurring phospholipids. Preferably, the synthetic phospholipids employed are 1-palmitoyl-2-oleoylphosphatidylcholine and 1-palmitoyl-2-oleoylphosphatidylserine.

In a preferred embodiment, the components of the mixture of POPC, POPS, and a selected phosphatidylalcohol, in this instance, dioleoylphosphatidylethanol (DOPETOH), are added and dissolved in a molar ratio of 70:15:15, respectively, in a suitable solution containing a detergent. In an alternative preferred embodiment, the components of the mixture are added in a molar ratio of 70:20:10, and in a further alternative preferred embodiment, the components are added in a molar ratio of 70:10:20. As an alternative to phosphatidylethanol, other preferred phosphatidylalcohols that are suitable for use in the present invention include dioleoylphosphatidylmethanol, dioleoylphosphatidylpropanol, dioleoylphosphatidylbutanol, and dioleoylphosphatidylinositol. The phosphatidylalcohols employed in the invention have negatively charged sites. While not wishing to be bound or limited by any theory, it is believed that the hydroxy or alcohol group protects the negatively charged sites to maintain repulsion between formed liposome particles.

The recombinant tissue factor, and a suitable carrier protein, such as bovine serum albumin (BSA), is added to a mixture of synthetic phospholipids including a phosphatidylalcohol that have been dissolved in an aqueous detergent solution. A preferred detergent for the detergent solution is octylglucoside (1-O-octyl-Dglucopyranoside), available from Sigma Chemical Co., of St. Louis, Mo., under Catalog No. 08001. Other detergents may be used in the solution, provided the concentration of micelles or liposomes in the detergent is high enough to permit solubilization of the phospholipids. For example, the concentration of the detergent in the solution is about 600 mM (as illustrated in Example 1) which concentration is effective to permit solubilization of the phospholipids. The detergent solution may further include about 0.1 mg/ml BHT, 14 mM Hepes, 0.1 M sodium chloride, 5% glycine (by weight), and 2% sorbitol (by weight), at a pH of 7.4. The concentration of the dissolved phospholipids in the detergent solution is about 12.76 mM.

The resulting mixture is incubated at room temperature for one hour with gentle shaking, and placed in a dialysis bag, and dialysed at 4° C. against a buffer solution of 14 mM Hepes, 0.1 M sodium chloride, 5% glycine (by weight), 2% sorbitol (by weight) at a pH of 7.4. The mixture is redialyzed against a buffer solution including 14 mM Hepes, 0.1 M sodium chloride, 5% serine (by weight) and 2% sorbitol (by weight) at a pH of 7.4. The combination of rabbit brain thromboplastin extract with glycine has been found to shorten the clotting times. See, Table 4, p. 555, data entry 3, of E. Hecht, et al., *Thrombosis et Diathesis Haemorrhagica*, Vol. 21, (3), pp. 546-560 (1960). The dialysed mixture is then drained from the bag and collected in a sterile polypropylene tube.

Although the detergent in the Examples is removed by dialysis (see e.g. L. T. Mimms, et al., "Phospholipid Vesicle Formation and Transmembrane Protein Incorporation Using Octyl Glucoside", Biochemistry, 20, 833-840 (1981), and R. Bach, et al., "Factor VII Bonding to Tissue Factor in Reconstituted Phospholipid Vesicles: Induction of Cooperativity by Phosphatidylserine", Biochemistry, 25, 40074020 (1986), the detergent may be removed by several methods known in the art to form a phospholipid tissue factor micelle. Suitable methods for detergent removal include, but are not limited to dialysis, diafiltration, ultrafiltration, and hydrophobic chromatography.

The resulting lipidated tissue factor is mixed with a formulation buffer. A preferred formulation buffer solution includes Hepes, sodium chloride, gammacyclodextrin, beta alanine, serine, sorbitol, bovine serum albumin, phenol, and butylatedhydroxytoluene. Gamma-cyclodextrin, or derivatives and analogs thereof, is added as a sensitivity adjuster for the reagent. The gamma-cyclodextrin employed is an aldehyde-free cyclic polymeric carbohydrate, and is added in an amount of about 1% by weight of the reagent. According to an aspect of the invention, the formulation buffer preferably includes 45 mM Hepes, 25 mM sodium chloride, 1% γ-cyclodextrin (by weight), 2% beta-alanine (by weight), 5% serine (by weight) 7% sorbitol by weight, 0.01% BSA (by weight), 0.005% phenol (by weight) and 0.00075% BHT (by weight).

Suitable carrier proteins function as a stabilizer for in vitro reactions, especially involving proteins. Although a suitable carrier protein for use in the present invention includes BSA, other suitable carrier proteins include, but are not limited to ovalbumin, and gamma globulin. Carrier proteins are used in a concentration of about 0.01 mg/ml to about 5.0 mg/ml. Preferably BSA is used at a concentration of about 0.01 mg/ml, and of about 0.2 mg/ml, and may be obtained from Sigma Chemical Co.

The reagent also may optionally contain a suitable antioxidant, particularly if air-drying of the reagent is desired. Antioxidants prevent the oxidation of the lipids to fatty acids. Suitable antioxidants include butylated hydroxytoluene (BHT), butylated hydroxyanisole (BHA), or Vitamin E, for example, in a concentration range of about 0.001 to 0.005% (by weight). Preferably, BHT is used at a concentration of about 0.01 mg/ml.

According to an aspect of the invention, the preferred buffer is Hepes, but other buffers may be used, including but not limited to MOPS (4-Morpholinepropanesulfonic acid), TES (2-[[tris(hydroxymethyl)methyl]amino]-1-ethanesulfonic acid), DIPSO (3[bis(2-hydroxyethyl)amino]-2-hydroxy-1-propanesulfonic acid), in a concentration range of 10 to 100 mM. Preferably the buffer used in the invention is Hepes at a concentration of about 14 mM.

A suitable salt for use in a Hepes buffer solution includes but is not limited to sodium chloride or potassium chloride, in a concentration range of about 0.005 to 0.2 M. Sodium chloride is preferably used in a concentration amount of between about 0.01 M and 0.10 M.

A suitable amino acid chelating agent is used such as serine, or threonine, in a concentration range of about 0.1 to 10% (by weight). Amino acid chelating agents can prevent precipitation by chelating contaminants or metal ions that may be present in the composition as a result of the formulation process. Preferably serine is used at about 4% to 6% (by weight).

One or more humectants are used, including but not limited to, glycerol (1,2,3-propanetriol), glycerol esters, sorbitol, ethylene glycol, propylene glycol, polyethylene glycol, in a total concentration range of about 1.0 to 10.0% (by weight). Preferably, sorbitol is used in a concentration range of about 5.0% to about 8.0% (by weight).

A humectant, such as sorbitol, is added to the reagent mixture to provide tackiness or stickiness upon air-drying the reagent. Although the mixture can be air-dried to a powder form, it has been found that the tackiness provided by a humectant is preferable when reconstituting the reagent. Moreover, the stickiness prevents the reagent from migrating within a test cuvette.

Suitable ionizable calcium sources for use with the present reagent and method of the invention where citrated blood is being assayed include, but are not limited to calcium salts of gluconate, acetate, or chloride in a preferred concentration of range of about 7.5 to about 14 mM. Calcium ions are essential for the activity of calcium dependent coagulation factors, such as Factors II, VII, IX and X. Calcium chloride is preferred as the calcium ion source, and is preferably added in about a 8 mM to about a 10 mM concentration.

Suitable biocides include e.g. phenol, and antibiotics such as penicillin or Kanamycin and the like which are added in an effective concentration range to inhibit biogrowth in the inventive composition. Phenol in the concentration range of about 0.005% to about 0.2% (by weight) is preferred.

The formulated material is air-dried without lyophilization at a temperature above about 20° C. to about 37° C. and a relative humidity of about 5% to about 10%, to yield a highly stable prothrombin time test reagent. Upon reconstitution with water, the reagent may be placed in various coagulation instruments for testing. For example, the air-dried reagent is reconstituted and placed in a cuvette of an MLA instrument for assay purposes, the ITC Hemochron Jr. Signature-Plus instrument from International Technidyne Corporation, or a Fibrometer.

Thus, the highly sensitive reagent is optimized for drying, preferably air-drying under ambient conditions. Rehydration of the reagent is rapid, and the stickiness of the reagent prevents the reagent from moving within the chosen test device prior to reconstitution. The reagent is highly stable. The air-dried reagent, maintained at a temperature of 37° C., remains stable for at least about three weeks.

Although the invention has been described with reference to the preferred embodiments thereof, it will be appreciated by those of ordinary skill in the art that modifications can be made to the parts that comprise the invention without departing from the spirit and scope thereof. The following examples will serve to further illustrate the invention but should not be construed as a limitation on the scope thereof, which is defined solely by the appended claims.

EXAMPLES

Example 1

Synthetic phospholipids, palmitoyloleoylphosphatidylcholine (POPC), palmitoyloleoylphosphatidylserine (POPS) and dioleoylphosphatidylethanol (DOPETOH) were dissolved at 45° C., respectively, in 600 mM octylglucoside (a detergent), 0.1 mg per ml butylated hydroxytoluene (BHT), 14 mM Hepes, 0.1 M sodium chloride, 5% glycine and 2% sorbitol, pH 7.4. The concentration of the dissolved phospholipids was 12.76 mM. The dissolved synthetic phospholipids were mixed with a molar ratio of POPC:POPS:DOPETOH (70:15:15). Bovine serum albumin (BSA) and recombinant rabbit brain tissue factor were added at a concentration of 0.06 mg/ml and 5.7 ug/ml, respectively. The mixture was incubated at room temperature for one hour with gentle shaking. Additional bovine serum albumin was added to make a concentration of 4.8 mg/ml. The mixture was then placed in a dialysis bag, and dialyzed at 4° C. against a buffer solution of 14 mM Hepes, 0.1 M sodium chloride, 5% glycine and 2% sorbitol, pH 7.4. The mixture was redialyzed against a buffer solution of 14 mM Hepes, 0.1 M sodium chloride, 5% serine and 2% sorbitiol to form a lipidated tissue factor. The dialyzed mixture, i.e., lipidated tissue factor, was then drained from the dialysis bag. The lipidated tissue factor was mixed with about 100-fold excess volume of a formulation buffer, which is composed of 45 mM Hepes, 25 mM sodium chloride, 1% γ-cyclodextrin, 2% β-alanine, 5% L-serine, 7% sorbitol, 0.01% bovine serum albumin (BSA), 0.005% phenol and 0.00075% butylated hydroxytoluene (BHT), pH 7.4. The formulated reagent was frozen at −75±5° C., and then thawed. The thawed formulated reagent was air-dried for two hours at 27° C. and 5% relative humidity.

The air-dried reagent was tested with fresh whole blood as a control, and fresh whole blood treated with low molecular weight heparin (Enoxaparin). The results are shown in Table 1-A. Citrated plasma may also be used for the assay. Normal pooled plasma of George King Corporation was mixed with saline-washed red blood cells (blood type "O") to 40% hematocrit to produce the state of citrated blood, calcium chloride was added to a final concentration of 8.3 mM, and the mixture was assayed with the air-dried PT reagent. (Table 1-B)

For accelerated stability studies, some of the air-dried reagent was incubated at 37° C. for 5 weeks. The reagent was taken out from the incubator at weekly intervals and subjected to coagulation assay using the Hemochron Jr. Signature-Plus instrument available from International Technidyne Corporation, Edison, N.J. The whole blood controls (normal and abnormal) used for the assay are also available from International Technidyne Corporation (Table 1-C).

TABLE 1-A

CLOTTING ASSAY OF FRESH WHOLE BLOOD TREATED WITH ENOXAPARIN

| Donor | [Enoxaparin] (units/ml) | Clotting Time (seconds) Trial 1 | Trial 2 | mean | 1.0/0.0 u/ml Ratio |
|---|---|---|---|---|---|
| 1 | 0.0 | 65 | 65 | 65.0 | — |
|   | 0.6 | 104 | 102 | 103.0 | 1.58 |
|   | 1.0 | 162 | 170 | 166.0 | 2.55 |
| 2 | 0.0 | 67 | 68 | 67.5 | — |
|   | 0.6 | 100 | 95 | 97.5 | 1.44 |
|   | 1.0 | 163 | 125 | 144.0 | 2.13 |
| 3 | 0.0 | 75 | — | 75.0 | — |
|   | 0.6 | 154 | 140 | 147.0 | 1.96 |
|   | 1.0 | 240 | 293 | 266.5 | 3.55 |
| 4 | 0.0 | 75 | 72 | 73.5 | — |
|   | 0.6 | 125 | 129 | 127.0 | 1.73 |
|   | 1.0 | 242 | 236 | 239.0 | 3.25 |
| 5 | 0.0 | 59 | 59 | 59.0 | — |
|   | 0.6 | 83 | 80 | 81.5 | 1.38 |
|   | 1.0 | 108 | 105 | 106.5 | 1.81 |
| 6 | 0.0 | 81 | 80 | 80.5 | — |
|   | 0.6 | 163 | 153 | 158.0 | 1.96 |
|   | 1.0 | 302 | 292 | 297.0 | 3.69 |
| 7 | 0.0 | 59 | 63 | 61.0 | — |
|   | 0.6 | 85 | 91 | 88.0 | 1.44 |
|   | 1.0 | 149 | 160 | 154.5 | 2.53 |
| 8 | 0.0 | 68 | 62 | 65.0 | — |
|   | 0.6 | 90 | 85 | 87.5 | 1.35 |
|   | 1.0 | 140 | 144 | 142.0 | 2.18 |

TABLE 1-A-continued

CLOTTING ASSAY OF FRESH WHOLE BLOOD TREATED WITH ENOXAPARIN

| Donor | [Enoxaparin] (units/ml) | Clotting Time (seconds) Trial 1 | Trial 2 | mean | 1.0/0.0 u/ml Ratio |
|---|---|---|---|---|---|
| 9 | 0.0 | 64 | 64 | 64.0 | — |
|  | 0.6 | 79 | 83 | 81.0 | 1.27 |
|  | 1.0 | 116 | 115 | 115.5 | 1.80 |
| 10 | 0.0 | 61 | 61 | 61.0 | — |
|  | 0.6 | 84 | 89 | 86.5 | 1.42 |
|  | 1.0 | 108 | 104 | 106.0 | 1.74 |

Average normal clot time = 67.15 seconds
Average one-unit clot time = 173.70 seconds
Sensitivity = 173.70/67.15 = 2.59

TABLE 1-B

CLOTTING ASSAY OF CITRATED NORMAL POOLED PLASMA MIXED WITH WASHED RED BLOOD CELLS AFTER ENOXAPARIN TREATMENT.

| Enoxaparin u/ml | Red Blood Cells from Blood Type "O" Donors | | | Mean (Seconds) |
|---|---|---|---|---|
|  | 1 | 2 | 3 |  |
|  | Clotting Time (Seconds) | | | |
| 0.0 | 75 | 74 | 77 | 75.3 |
| 0.2 | 87 | 86 | 89 | 87.3 |
| 0.4 | 111 | 115 | 114 | 113.3 |
| 0.6 | 147 | 140 | 157 | 148.0 |
| 0.8 | 206 | 205 | 209 | 206.7 |
| 1.0 | 255 | 235 | 265 | 251.7 |

TABLE 1-C

STABILITY OF LOW MOLECULAR WEIGHT HEPARIN ASSAY REAGENT

| Incubation days | Temp. (° C.) | Normal Control* Seconds | Abnormal Control** Seconds |
|---|---|---|---|
| 0 | 25 | 74 | 116 |
| 7 | 37 | 73 | 117 |
| 14 | 37 | 75 | 118 |
| 21 | 37 | 77 | 125 |
| 28 | 37 | 78 | 128 |
| 35 | 37 | 76 | 127 |

*Whole blood normal control of International Technidyne Corporation (Catalog No. DCJ-N)
**Whole blood abnormal control of International Technidyne Corporation (Catalog No. DCJPT-A).

Example 2

The composition of phospholipids (POPC/POPS=7:3) and recombinant rabbit brain tissue factor, 42.5 µg/ml, as described in U.S. Pat. No. 6,183,979 to Lee et al., were used in the lipidation of tissue factor, and test reagent was prepared by the method described in Example 1. Enoxaparin treated fresh whole blood sample was tested with the prepared air-dried reagent as in Example 1. The separation of clotting times between 0.0 and 1.0 u/ml was very narrow to use this composition of phospholipids and recombinant tissue factor (Table 2) for Enoxaparin assay in whole blood. Using the same phospholipid composition (POPC/POPS=7:3) and a lower concentration of recombinant rabbit brain tissue factor, 5.6 µg/ml, did not improve the results.

TABLE 2

|  | rTF (µg/ml) in lipidation | Enoxaparin, u/ml | |
|---|---|---|---|
|  |  | 0.0 | 1.0 |
|  |  | Clotting Time (Seconds) | |
| POPC:POPS (7:3) | 42.5 | 26 | 30 |
| POPC:POPS (7:3) | 5.6 | 26 | 32 |

Example 3

The ethanol group in the dioleoylphosphatidylethanol (DOPETOH) in Example 1 was substituted with other aliphatic alchohols, namely, methanol, propanol, butanol, and inositol. The other phospholipids and formulation buffer solutions were the same as in Example 1. The ratio of POPC:POPS:dioleoylphosphatidyl alcohol was 70:15:15, as was in Example 1. The reagents prepared with methanol, propanol, butanol and inositol conjugated with dioleoylphosphatidyl group provided results (Table 3) very similar to the reagent prepared with dioleoylphosphatidylethanol when assayed with fresh whole blood mixed with Enoxaparin. In this example, citrated blood was used. Calcium chloride was added to the citrated blood sample to a final concentration of 8.3 mM, and each blood sample was assayed immediately as in Example 1.

TABLE 3

| Dioleoylphosphatidylalcohol | Enoxaparin (u/ml) | | | Sensitivity Clotting time ratio of 1.0/0.0 u/ml |
|---|---|---|---|---|
|  | 0.0 | 0.6 | 1.0 |  |
|  | Clotting Time (Seconds) | | | |
| Dioleoylphosphatidylethanol | 63 | 99 | 163 | 2.59 |
| Dioleoylphosphatidylmethanol | 70 | 119 | 161 | 2.30 |
| Dioleoylphosphatidylpropanol | 63 | 89 | 155 | 2.46 |
| Dioleoylphosphatidylbutanol | 69 | 124 | 162 | 2.35 |
| Dioleoylphosphatidylinositol | 82 | 166 | 215 | 2.62 |

Example 4

The ratio of POPC:POPS:DOPETOH in Example 1 (70:15:15) was changed to 70:20:10 and 70:10:20 to estimate the usable concentration range of POPS and DOPETOH for the preparation of the test reagent for low molecular weight heparin assay. The formulation solution used, and air-drying of the reagent was the same as in Example 1. Clotting assays were conducted as described in Example 1 with fresh whole blood mixed with Enoxaparin. The results are shown in Table 4.

TABLE 4

| The concentration ratio of POPC:POPS:DOPETOH | Enoxaparin (u/ml) | | Clotting Time |
|---|---|---|---|
|  | 0.0 | 1.0 | Ratio |
|  | Clotting Time (seconds) | | 1.0/0.0 u/ml |
| 70:15:15 | 67 | 174 | 2.6 |
| 70:20:10 | 60 | 132 | 2.2 |
| 70:10:20 | 129 | 389 | 3.0 |

Example 5

The DOPETOH of Example 1 was replaced with Palmitoyloleoylphosphatidic acid (POPA). The rest of the reagent preparation, air-drying and clotting assay were done as in Example 1. The clotting assay results (Table 5) showed that the POPA containing preparation was not as sensitive as the DOPETOH containing reagent, and the clotting times changed after 2 days of incubation at 37° C. The data indicates that DOPETOH performed better than POPA in the preparation of assay reagent for low molecular weight heparin.

TABLE 5

| The concentration ratio of POPC:POPS:POPA (70:15:15) | Enoxaparin (u/ml) 0.0 Clotting Time (seconds) | 1.0 | Sensitivity Clotting time ratio of 1.0/0.0 u/ml |
|---|---|---|---|
| Freshly prepared | 64 | 108 | 1.69 |
| After 2 days at 37° C. | 73 | 150 | 2.05 |

Example 6

The concentration of some of the formulation compounds used in the Example 1 (sorbitol, sodium chloride, L-serine, beta-alanine, and γ-cyclodextrin) were varied. The prepared reagents were air-dried, and the clotting activity of an Enoxaparin treated whole blood sample obtained from a donor was measured with these reagents. The results are shown in Table 6. Out of these five chemical compounds tested for their concentration effect on clotting times, γ-cyclodextrin appeared to have a stronger effect. This part of the study was extended in Example 7.

TABLE 6

| Component varied | | Enoxaparin (u/ml) | Clot Time (Sec.) |
|---|---|---|---|
| Control* | | 0.0 | 64 |
| Control* | | 1.0 | 155 |
| Sodium Chloride | 10 mM | 0.0 | 62 |
| Sodium Chloride | 10 mM | 1.0 | 147 |
| Sorbitol | 5.0% | 0.0 | 60 |
| Sorbitol | 5.0% | 1.0 | 168 |
| Sorbitol | 8.0% | 0.0 | 60 |
| Sorbitol | 8.0% | 1.0 | 137 |
| Serine | 4.0% | 0.0 | 59 |
| Serine | 4.0% | 1.0 | 131 |
| Serine | 6.0% | 0.0 | 68 |
| Serine | 6.0% | 1.0 | 158 |
| β-Alanine | 1.5% | 0.0 | 61 |
| β-Alanine | 1.5% | 1.0 | 123 |
| β-Alanine | 3.0% | 0.0 | 65 |
| β-Alanine | 3.0% | 1.0 | 153 |
| γ-Cyclodextrin | 0.5% | 0.0 | 59 |
| γ-Cyclodextrin | 0.5% | 1.0 | 100 |
| γ-Cyclodextrin | 2.0% | 0.0 | 90 |
| γ-Cyclodextrin | 2.0% | 1.0 | >300 |

*The control was prepared with the formulation solution described in Example 1: 25 mM sodium chloride, 7% sorbitol, 5% serine, 2% β-Alanine, 1% γ-Cyclodextrin, 45 mM Hepes, 0.01% BSA, 0.005% phenol, 0.00075% BHT, pH 7.4.

Example 7

The concentration of γ-Cyclodextrin in the formulation solution was varied was from 0.0 to 2.0% (w/v) to determine the effect of this compound on the sensitivity of the low molecular heparin assay. The reagent preparation, air-drying and testing of fresh whole blood were the same as in Example 1, except that γ-Cyclodextrin was varied in the formulation solution. The results (Table 7) show that γ-Cyclodextrin is a very effective sensitivity adjuster for low molecular heparin assay.

TABLE 7

| γ-Cyclodextrin concentration (%) | Enoxaparin (u/ml) 0.0 Clotting Time (seconds) | 1.0 | Sensitivity (Clotting time ratio of 1.0/0.0 u/ml) |
|---|---|---|---|
| 0.0 | 51 | 74 | 1.5 |
| 0.5 | 59 | 100 | 1.7 |
| 1.0 | 64 | 152 | 2.4 |
| 1.5 | 70 | 241 | 3.4 |
| 2.0 | 90 | >300 | — |

Example 8

Dalteparin was tested following the procedure described in Example 1. Fresh whole blood was treated with 0.0, 0.6 and 1.0 unit of Dalteparin per ml of blood, and tested. The results are shown in Table 8.

TABLE 8

| | u/ml | | |
|---|---|---|---|
| Low molecular weight heparin | 0.0 | 0.6 | 1.0 |
| | Clotting Time (Seconds) | | |
| Enoxaparin | 65 | 103 | 166 |
| Dalteparin | 62 | 118 | 219 |

What is claimed is:

1. A prothrombin time reagent for determining the concentration of low molecular weight heparin in fresh whole blood and anti-coagulant-treated blood comprising:
   a recombinant animal tissue factor;
   a mixture of synthetic phospholipids including a selected phosphatidylalcohol, which mixture lipidates said recombinant animal tissue factor to form a lipidated tissue factor; and
   a buffer solution comprising Hepes, sodium chloride; gamma-cyclodextrin; beta-alanine; serine; sorbitol; bovine serum albumin; phenol; and butylated hydroxytoluene, and wherein the reagent is exposed in an atmosphere of about 5% to about 10% relative humidity at about 20° C. to about 37° C. to thereby form an air-dried reagent.

2. The reagent according to claim 1, wherein said reagent is stable for at least three weeks at a temperature of about 37° C.

3. A prothrombin time reagent for determining the concentration of low molecular weight heparin in fresh whole blood and anti-coagulant-treated blood comprising:
   a recombinant animal tissue factor comprising rabbit brain; and
   a mixture of synthetic phospholipids including a selected phosphatidylalchol, which mixture lipidates said recombinant animal tissue factor to form a lipidated tissue factor; and wherein said recombinant animal tissue factor comprising rabbit brain is present in an amount of about 4 µg/ml to about 6 µg/ml.

4. A protbrombin time reagent for determining the concentration of low molecular weight heparin in fresh whole blood and anticoagulant-treated blood, comprising:
   a recombinant animal tissue factor;
   a mixture of synthetic phospholipids including a selected phosphatidylalcohol, which mixture lipidates said tissue factor to form a liposome complex; and
a buffer solution comprising an aldehyde-free gamma-cyclodextrin sensitivity adjuster.

5. The reagent according to claim 4, wherein said recombinant animal tissue factor comprises rabbit brain.

6. The reagent according to claim 5, wherein said recombinant animal tissue factor comprising rabbit brain is present in an amount of about 4 μg/ml to about 6 μg/ml.

7. The reagent according to claim 4, wherein said mixture of synthetic phospholipids further comprises palmitoyloleoylphosphatidylcholine (POPC) and palmitoyoleoylphosphatidylserine (POPS).

8. The reagent according to claim 7, further comprising a concentration ratio of 70:10 to 20:10 to 20 for said mixture of POPC, POPS, and said selected phosphatidylalcohol.

9. The reagent according to claim 8, wherein said selected phosphatidylalcohol is selected from the group consisting of:
   dioleoylphosphatidylethanol, dioleoylphosphatidylmethanol, dioleoylphosphatidylpropanol, dioleoylphosphatidylbutanol, and dioleoylphosphatidylinositol.

10. The reagent according to claim 4, wherein said buffer solution further comprises
   Hepes, sodium chloride; beta-alanine; seine; sorbitol; bovine serum albumin; phenol; and butylated hydroxytoluene.

11. The reagent according to claim 4, wherein the reagent is exposed in an atmosphere of about 5% to about 10% relative humidity at about 20° C. to about 37° C. for about two hours to thereby form an air-dried reagent.

12. The reagent according to claim 4, wherein said sensitivity adjuster is present in an amount of about 1% by weight of the reagent.

13. The reagent according to claim 11, wherein the air dried reagent remains stable for at least about three weeks at about 37° C.

* * * * *